United States Patent
Laudanski et al.

(10) Patent No.: US 9,584,928 B2
(45) Date of Patent: Feb. 28, 2017

(54) BILATERAL HEARING ASSISTANCE SYSTEM AND A METHOD OF FITTING A BILATERAL HEARING ASSISTANCE SYSTEM

(71) Applicants: Oticon Medical A/S, Smørum (DK); University College London, London (GB)

(72) Inventors: Jonathan Laudanski, Vallauris (FR); Jamie A. Undurraga, London (GB); Nick Haywood, London (GB); Torsten Marquardt, London (GB); David McAlpine, London (GB)

(73) Assignees: OTICON MEDICAL A/S, Smorum (DK); UNIVERSITY COLLEGE LONDON, London (GB)

( * ) Notice: Subject to any disclaimer, the term of this patent is extended or adjusted under 35 U.S.C. 154(b) by 9 days.

(21) Appl. No.: 14/643,724

(22) Filed: Mar. 10, 2015

(65) Prior Publication Data
US 2015/0264492 A1 Sep. 17, 2015

(30) Foreign Application Priority Data

Mar. 11, 2014 (EP) .................................... 14158959

(51) Int. Cl.
*H04R 29/00* (2006.01)
*H04R 25/00* (2006.01)
(Continued)

(52) U.S. Cl.
CPC ......... *H04R 25/30* (2013.01); *A61B 5/04845* (2013.01); *H04R 1/10* (2013.01);
(Continued)

(58) Field of Classification Search
CPC ................ A61K 2300/00; A61K 45/06; A61K 31/7088; A61K 35/28; A61K 35/30;
(Continued)

(56) References Cited

U.S. PATENT DOCUMENTS 6,428,484 B1 8/2002 Battmer et al.
2005/0245991 A1* 11/2005 Faltys .................... H04R 25/70
607/57
(Continued)

FOREIGN PATENT DOCUMENTS

EP 1 522 208 A1 4/2005
EP 1 522 208 B1 9/2010
(Continued)

OTHER PUBLICATIONS

Dajani et al., "Human auditory steady-state responses to changes in interaural correlation," Hearing Research, 2006, vol. 219, pp. 85-100.
(Continued)

*Primary Examiner* — Lun-See Lao
(74) *Attorney, Agent, or Firm* — Birch, Stewart, Kolasch & Birch, LLP

(57) ABSTRACT

The application relates to a bilateral hearing assistance system comprising first and second hearing assistance devices a processing unit, which in a NORMAL mode of operation processes an input audio signal based on configurable processing parameters and provides a processed electric stimulation signal. The system further includes one or more stimulation units for—in a TEST mode delivers first and second electric TEST stimulation signals to output units of said first and second devices respectively. The application further relates to a method of fitting a bilateral hearing assistance system to a particular user. The disclosure provides a measure allowing an improved fitting of bilaterally
(Continued)

implanted Cochlear Implant users. The system further includes an evaluation unit configured to analyze the recorded physiological response of the user and to provide an objective measure of the user's perception of said TEST stimulation signals.

19 Claims, 8 Drawing Sheets

(51) Int. Cl.
  *A61B 5/0484* (2006.01)
  *H04R 1/10* (2006.01)
  *A61B 5/12* (2006.01)
(52) U.S. Cl.
  CPC .......... *H04R 25/606* (2013.01); *H04R 25/70* (2013.01); *A61B 5/125* (2013.01)
(58) Field of Classification Search
  CPC .. A61K 38/1709; A61K 39/395; A61K 35/12; A61K 35/18; A61K 35/19; A61K 35/32; A61K 35/39; A61K 38/19; A61K 39/39558; A61K 2035/124; H04R 1/10; H04R 25/30; H04R 25/552; H04R 25/554; H04R 25/558; H04R 25/606; H04R 25/70; H04S 2400/01; H04S 2420/01; H04S 5/00; H04W 12/02; H04W 12/12; H04W 24/10; H04W 36/0022; H04W 36/14; H04W 36/30; H04W 36/36; H04W 52/0229; H04W 52/0251
  USPC 381/60, 1, 312, 317, 300, 309, 311, 74, 58; 600/25, 500; 607/55, 137
  See application file for complete search history.

(56) References Cited

U.S. PATENT DOCUMENTS

| | | | |
|---|---|---|---|
| 2006/0015155 A1 | 1/2006 | Charvin et al. | |
| 2006/0100672 A1 | 5/2006 | Litvak | |
| 2006/0215845 A1* | 9/2006 | Burleigh | A61B 5/00 381/60 |
| 2006/0287690 A1* | 12/2006 | Bouchataoui | H04R 25/606 607/57 |
| 2009/0254149 A1* | 10/2009 | Polak | A61B 5/121 607/57 |
| 2011/0295166 A1* | 12/2011 | Dalton | A61B 5/04845 601/47 |
| 2015/0018699 A1* | 1/2015 | Zeng | A61B 5/04001 600/509 |

FOREIGN PATENT DOCUMENTS

| | | |
|---|---|---|
| WO | WO 2013/116161 A1 | 8/2013 |
| WO | WO 2013/142843 A1 | 9/2013 |

OTHER PUBLICATIONS

Dobie et al., "Binaural Interaction in Human Auditory Evoked Potentials," Electroencephalography and Clinical Neurophysiology, 1980, vol. 49, pp. 303-313.
Fowler et al., "Frequency Dependence of Binaural Interaction in the Auditory Brainstem and Middle Latency Responses," American Journal of Audiology, Dec. 2012, vol. 21, pp. 190-198.
He et al., "Preliminary Results of the Relationship Between the Binaural Interaction Component of the Electrically Evoked Auditory Brainstem Response and Interaural Pitch Comparisons in Bilateral Cochlear Implant Recipients," Ear & Hearing, 2012, vol. 33, No. 1, pp. 57-68.
Hofmann et al., "Electrically Evoked Auditory Steady State Responses in Cochlear Implant Users," Association for Research in Otolaryngology, 2010, pp. 267-282.
Ishida et al., "Does the 40-Hz Auditory Steady-State Response Show the Binaural Masking Level Difference?," Ear & Hearing, 2009, vol. 30, No. 6, pp. 713-715.
Maki et al., "Effects of Contralateral Noise on 40-Hz and 80-Hz Auditory Steady-State Responses," Ear & Hearing, 2009, vol. 30, No. 5, pp. 584-589.
Massoud et al., "Sensitivity of the Human Binaural Cortical Steady State Response to Interaural Level Differencese," Ear & Hearing, 2011, vol. 32, No. 1, pp. 114-120.
Riedel et al., "Interaural delay-dependent changes in the binaural difference potential of the human auditory brain stem response," Hearing Research, 2006, vol. 218, pp. 5-19.
Ross et al., "Physiological detection of interaural phase differences," The Journal of the Acoustical Society of America, Feb. 2007, vol. 121, No. 2, pp. 1017-1027.
Ross., "A Novel Type of Auditory Responses: Temporal Dynamics of 40-Hz Steady-State Responses Induced by Changes in Sound Localization," Journal of Neurophysiology, Sep. 2008, vol. 100, pp. 1265-1277.
Smith et al., "Sensitivity of Inferior Colliculus Neurons to Interaural Time Differences in the Envelope Versus the Fine Structure With Bilateral Cochlear Implants," Journal of Neurophysiology, May 2008, vol. 99, pp. 2390-2407.
van Hoesel et al., "Sensitivity to binaural timing in bilateral cochlear implant users," Journal of the Acoustical Society of America, Apr. 2007, vol. 121, No. 4, pp. 2192-2206.

\* cited by examiner

BILATERAL HEARING ASSISTANCE SYSTEM AND A METHOD OF FITTING A BILATERAL HEARING ASSISTANCE SYSTEM

TECHNICAL FIELD

The present application relates to fitting of hearing assistance devices, in particular to such devices comprising an implanted multi-channel electrode array. The disclosure relates specifically to a bilateral hearing assistance system and to a method of measuring a physiological response to a bilateral stimulation.

The application furthermore relates to a fitting system and to a method of fitting a bilateral hearing assistance system, in particular to system comprising at least one cochlear implant hearing assistance device.

Embodiments of the disclosure may e.g. be useful in applications such as fitting of hearing assistance devices comprising cochlear implants.

BACKGROUND

Patients with impaired hearing may be offered the implantation of a stimulating multi-channel electrode array into each cochlea (bilateral implantation), or the combination of a single cochlear implant with a hearing aid in the opposite ear (bimodal system). In both cases, through binaural stimulation the patient may experience both improved speech perception and source localization (relative to unilateral stimulation/hearing). Recent research suggests that patients using bilateral or bimodal systems will receive maximum benefit to binaural hearing if incoming sounds stimulate similar locations along the cochlea in both ears. In the case of bilateral implantation, this means that a sound should stimulate a well matched pair of electrodes (i.e., the responding electrodes in the left and right ear should each stimulate comparable cochlea regions). Research from normal hearing listeners, or electrical stimulation in animal models, suggests that auditory evoked potentials could be used to measure binaural processing. In general terms, three different types of binaural responses have been measured:
1. Binaural interaction component: (cf. e.g. [Dobie & Norton, 1980], [Riedel & Kollmeier, 2006], [Smith and Delgutte, 2008], [He, Brown, & Abbas, 2012], or [Fowler & Horn, 2012]).
2. Auditory steady-state response (cf. e.g. [Maki, Kawase, & Kobayashi, 2009] or [Ishida & Stapells, 2009]).
3. Late evoked potentials (cf. e.g. [Dajani & Picton, 2006], [Massoud et al., 2011], [Ross, Tremblay & Picton, 2007], or [Ross, 2008]).

US2006100672A1 deals with systems and methods for matching pitch information between bilateral cochlear implants in order to maximize a patient's listening experience. The system permits an electrode array of a first cochlear implant to be pitch matched to an electrode array of a second cochlear implant system by utilizing virtual electrodes, which enable cochlear stimulation at a location in between physical electrodes on the electrode array. At least one electrode of the first electrode array is mapped to a virtual electrode of the second electrode array.

US20090254149A1 describes an objective measurement of cochlear implant operation which coordinates the delivery to a patient of an acoustic signal and an electrical signal. The acoustic signal is developed as an acoustic stimulation input to the ear canal of a patient, and the electrical signal is developed as an electrical stimulation input to intracochlear electrodes of a cochlear implant. The evoked response in the patient to the delivered signals is then measured.

In the present context, a bilateral hearing assistance system is intended to comprise a hearing assistance device-pair (first and second hearing assistance devices) adapted for being worn at or in, or partially or fully implanted in the head at, left and right ears of a user, respectively. The hearing assistance device-pair may be lacking the capability of exchanging data between them. Alternatively, the hearing assistance device-pair may be adapted to be able to exchange data between them, 'data' being audio signals, control signals (such as the frequency allocation map), and/or other parameters (such as the relative timing between signal in each ears).

SUMMARY

There is a need for an objective measure to assess binaural processing.

For implanted patients, the measurement of binaural processing with auditory evoked potentials may provide a time-efficient and clinically suitable means to define the temporal and tonotopic parameters that provide best binaural benefit to a patient. We propose a system to objectively measure binaural processing by recording evoked potentials. This system may allow bilateral or bimodal patients to receive improved benefits to both speech perception and source localization, through the improved temporal/place matching of stimulation electrode(s).

Embodiments of the present disclosure deal with measuring a frequency following response (FFR) of a user to abrupt interaural phase changes (IPC, =>FFR-IPCs) imposed on amplitude modulated signals.

The present application provides a measure allowing an improved fitting of bilaterally implanted CI users. An embodiment of the present disclosure is to provide an objective measure to assess processing in bilateral cochlear implant hearing assistance systems. The disclosure further provides a matching of binaural signals in a bilateral hearing assistance system. A further object of the present disclosure is to provide a matching procedure that is more precisely (objectively) defined.

The disclosure is implemented in accordance with the accompanying claims and as described in the following.

A Bilateral Hearing Assistance System:

In an aspect of the present application, the disclosure is implemented by a bilateral hearing assistance system comprising a control unit and first and second hearing assistance devices, each of the first and second hearing assistance devices
  being adapted for being located at or in an ear of the user or to be partially or fully implanted in the head at an ear of the user, and
  comprising an output unit adapted to present a stimulation signal to said user in a form allowing it to be perceived by the user as an auditory signal,
the bilateral hearing assistance system further comprising
  one or more stimulation units for—in a TEST mode of operation of the hearing assistance system—delivering first and second electric TEST stimulation signals to said output units of said first and second hearing assistance devices, respectively.

The bilateral hearing assistance system further comprises,
  a recording unit configured to record the user's physiological response to said first and/or second electric TEST stimulation signals; and an evaluation unit being configured to analyze the recorded physiological response of the user and to provide an objective measure of the user's perception of said TEST stimulation signals.

An advantage of the present disclosure is that it provides an objective scheme for identifying the quality of perception of binaural signals in a bilateral hearing assistance system.

The term 'in a form allowing it to be perceived by the user as an auditory signal' is in the present context taken to include 'being configured to provide electrical, mechanical or acoustic stimulation of the auditory system of the user', as the case may be.

The term 'physiological response' to said first and/or second electric TEST stimulation signals is in the present context taken to mean the response evoked in the user's body by the stimulation signals. Such 'physiological' or 'evoked' responses can e.g. be captured as nerve responses or brain wave signals in the form of electrical potentials from a user's nervous system by recording electrodes. The recording electrodes may be located internally in the head of the user or be external electrodes attached to the skin (e.g. of the scalp or in an ear canal) of the user. Such evoked responses can e.g. be in the form of acoustically evoked potentials (AEP) or electrically evoked potentials, the latter being sometimes referred to as 'electrically evoked auditory potentials' (EAP), or electrically evoked compound action potentials (eCAPs), or electrically evoked auditory brain stem responses (eABRs).

In an embodiment, each of said first and second electric TEST stimulation signals are defined by respective first and second stimulation parameters, respectively.

The control unit is preferably connectable to the one or more stimulation units in the specific TEST mode of operation. In an embodiment, the control unit is configured to control the first and second electric stimulation signals. In an embodiment, the control unit is configured to change the first and/or second electric stimulation signals by changing respective first and second stimulation parameters. In an embodiment, the change of the first and/or second electric stimulation signals is made in dependence of the objective measure of the user's perception of the stimulation signals. In an embodiment, the control unit is configured to control the initiation of the first and second electric stimulation signals. In an embodiment, the control unit is configured to control the mutual difference in time of initiation of the first and second electric stimulation signals. In an embodiment, the control unit is configured to change a mutual timing of the initiation of said first and second electric stimulation signals. In an embodiment, the control unit is adapted to provide that the change of the mutual timing is made in dependence of said objective measure of the user's perception of said stimulation signals.

In an embodiment, the control unit is connected to the recording device. In an embodiment, the control unit is configured to modify either the first or the second stimulation parameters, respectively, or both at the same time.

In an embodiment, the bilateral hearing assistance system comprises a processing unit, which in a NORMAL mode of operation is adapted to process an input audio signal based on configurable processing parameters and to provide a processed electric stimulation signal to respective output units of the first and second hearing assistance devices. In an embodiment, the first and second hearing assistance devices are controlled by the same processing unit. Preferably, the processing unit is adapted to allow individual (possibly different) processing parameters to be applied to the respective first and second hearing assistance devices. In an embodiment, each of the first and second hearing assistance devices comprise a processing unit that is adapted to process an input audio signal based on configurable processing parameters and to provide a processed electric stimulation signal to said output units of the first and second hearing assistance devices, respectively.

In an embodiment, the control unit is fully or partially implemented in a processing unit (e.g. a speech processor) in one of the first or second hearing assistance devices (e.g. a cochlear implant device). Alternatively, the control unit may be fully or partly implemented in a fitting system or in a diagnostic apparatus, e.g. of the recording unit.

In an embodiment, each of the first and second hearing assistance devices comprises a processing unit, which in a NORMAL mode of operation is adapted to process an input audio signal based on configurable processing parameters and to provide a processed electric stimulation signal.

In an embodiment, the bilateral hearing assistance system (e.g. the control unit) is configured to modify the configurable processing parameters of the first and/or second hearing assistance devices based on said objective measure of the user's perception of said TEST stimulation signals.

In an embodiment, the control unit is configured to exchange data with said first and second hearing assistance devices. In an embodiment, the control unit is configured to control a mode of operation of the first and second hearing assistance devices. In an embodiment, the first and second hearing assistance devices are configured to be able to operate in at least a normal mode and a test mode.

In an embodiment, the recording unit is connectable to or comprises a capture system for recording (acquiring) the physiological response of the user to said first and second electric stimulation signals. In an embodiment, the recording unit is connected to or comprises an electrophysiological acquisition device, and/or recording electrodes placed on the scalp, in an ear canal or in the head of the user: In an embodiment, the electrophysiological device is configured to record the patient's physiological response in a synchronized manner fashioned to either ipsi-lateral, contra-lateral, or bilateral stimulation. In an embodiment, the electrophysiological device comprises an external acquisition system, which uses recording electrodes placed on the scalp of the user to record small electrophysiological signals (such as an ABR or EEG system). In an embodiment, the electrophysiological device comprises an internal acquisition system, which is part of the stimulating device (such as an eCAP measurement system). In an embodiment, the electrophysiological device comprises implanted, extra-cochlear electrodes, cf. e.g. U.S. Pat. No. 6,428,484. In an embodiment, the electrophysiological device comprises a combination of an external and an internal acquisition system.

In an embodiment, the bilateral hearing assistance system comprises a user interface allowing a user to influence or control the functionality of the hearing assistance system (e.g. the control unit), e.g. to change a mode of operation, initiate a stimulation and subsequent recording of evoked responses, choosing stimulation signals, view result of objective measures, change processing parameters of the processing units of the first and/or second hearing assistance devices, etc.

In an embodiment, the first hearing assistance device comprises
   a first implanted part adapted for being implanted in an ipsi-lateral side of the user's head, the implanted part comprising the output unit of the first hearing assistance device, and wherein said output unit comprises a first multi-channel electrode array adapted for being located in proximity of neurons of the auditory system of the user; and a first electrode control unit configured to provide that a specific electrode in the first multi-channel electrode array is stimulated by said first electric TEST stimulation signal, In an embodiment, the second hearing assistance device comprises a second implanted part adapted for being implanted in a contra-lateral side of the user's head, the implanted part comprising the output unit of the second hearing assistance device, and wherein said output unit comprises a second multi-channel electrode array adapted for being located in proximity of neurons of the auditory system of the user; and a second electrode control unit configured to provide that a specific electrode in the first multi-channel electrode array is stimulated by said second electric TEST stimulation signal.

In an embodiment, the second hearing assistance device comprises an ear piece adapted for being located in or at an ear at a contra-lateral side of the user's head, the ear piece comprising the output unit of the second hearing assistance device, said output unit being adapted for converting said second electric TEST stimulation signal to an output sound and playing said output sound into the ear of the user.

In an embodiment, the (first) hearing assistance device on the ipsi-lateral side is a cochlear implant type device, and the (second) hearing assistance device on the contra-lateral side is an auditory brainstem implant (ABI) device. In an embodiment, the (first) hearing assistance device on the ipsi-lateral side is an auditory brainstem implant device, and the (second) hearing assistance device on the contra-lateral side is an auditory brainstem implant device.

In an embodiment, the first and second electric TEST stimulation signals each comprise a train of pulses. In an embodiment, the control unit is adapted to control the relative timing of the pulse trains arriving at the two multi-channel array electrodes of respective cochlear implant hearing assistance devices, or the relative timing between the simulating sound (sound phase) and the electric pulse train (electric phase) or respective air conduction and cochlear implant hearing assistance devices. Preferably, the first and second electric TEST stimulation signals are fully described by a first and second set of stimulation parameters, respectively. In an embodiment, the control unit is configured to update stimulus parameters based on recorded evoked physiological response to periodic rapid transitions in the relative timing of the stimulation to each ear. Alternatively, the stimulus parameters may be updated according to a predefined algorithm (e.g. to go through a range of relative timing differences between the signals presented at the ipsi- and contra-lateral hearing assistance devices with a predefined step length), or an adaptive algorithm. As an example, a stimulus may alternate between having the same arrival time in both ears and having a delayed arrival time in one ear relative to the other. Different values of interaural timing difference may thus emulated. The scheme is applicable whether the stimulation is either acoustical or electrical. In an embodiment, the control unit is configured to change either the parameters of the frequency distribution allocated to each electrodes in the ipsi or contra-lateral case. In an embodiment, the control unit is configured to set a minimal Interaural Time Difference (ITD) for the binaural processing that the processing unit speech processor would automatically assign to sound sources.

In an embodiment, the bilateral hearing assistance system comprises or is connectable to a fitting system, allowing the modification of parameters of the processor units of the first and/or second hearing assistance devices in accordance with the results of the recording (the objective measure) and an algorithm established in the method of fitting.

Use:

In an aspect, use of a bilateral hearing assistance system as described above, in the 'detailed description of embodiments' and in the claims, is moreover provided. In an embodiment, use is provided in a system comprising at least one cochlear implant hearing assistance device comprising a multi-channel electrode array. In an embodiment, use is provided in a fitting system for fitting a pair of hearing assistance devices, e.g. a pair of cochlear implant hearing assistance devices to a particular user.

A Method:

In an aspect, a method of fitting a bilateral hearing assistance system to a particular user, the bilateral hearing assistance system comprising first and second hearing assistance devices, each being adapted for being located at or in an ear of the user or to be partially or fully implanted in the head at an ear of the user, each of the first and second hearing assistance devices being configured to allow electrical, mechanical or acoustic stimulation of the auditory system of the user is furthermore provided by the present application. The method comprises generating first TEST stimuli (e.g. defined by a first set of parameters) to the auditory system at an ipsi-lateral side of the user's head;

generating second TEST stimuli (e.g. defined by a second set of parameters) to the auditory system at a contra-lateral side of the user's head;

recording the user's physiological response to either ipsi-lateral, contra-lateral, or bilateral stimulation; and evaluating the recorded physiological responses of the user to extract information about the current fitting of the first and second hearing assistance devices.

It is intended that some or all of the structural features of the system described above, in the 'detailed description of embodiments' or in the claims can be combined with embodiments of the method, when appropriately substituted by a corresponding process and vice versa. Embodiments of the method have the same advantages as the corresponding systems.

In an embodiment, the method comprises adapting processing parameters of the first and second hearing assistance devices based on the extracted information about the current fitting of the first and second hearing assistance devices (e.g. an objective measure of a user's perception of the applied first and second stimuli).

In an embodiment, the first and second hearing assistance devices each comprises a cochlear implant hearing assistance device. In an embodiment, the first hearing assistance devices comprises a cochlear implant hearing assistance device and the second hearing assistance devices comprises an air conduction or a bone conduction hearing assistance device.

In an embodiment, the first and second stimuli each comprise a train of (e.g. electric) pulses. In an embodiment, the first stimuli comprise a train of electric pulses and the second stimuli comprise a train of acoustic pulses.

In an embodiment, the strength or the phase or both strength and phase of a steady-state auditory response produced by the binaural signals is used to assess the optimality of the binaural fitting parameters.

In an embodiment, the steady-state electrophysiological response indicates that a place-mismatch exists between the TEST signal in the first ear and the second signal in the contra-lateral ear. In an embodiment, the steady-state electrophysiological response indicates that a minimal time-delay between the TEST signal in the first ear and the signal in the contra-lateral ear exists. In an embodiment, such minimal time delay is subsequently used to modify the fitting parameters of the binaural processing unit. In an embodiment, the steady-state electrophysiological response indicates that a maximal time-delay between the TEST signal in the first ear and the signal in the contra-lateral ear exists. In an embodiment, such maximal time delay is subsequently used to modify the fitting parameters of the binaural processing unit.

In an embodiment, the first and second electric TEST stimulation signals comprise abrupt interaural phase changes (IPCs) imposed on amplitude modulated signals and where the recording of the user's physiological response comprises recording the Frequency Following Response to said Interaural Phase Changes (FFR-IPC). In an embodiment, the phase of the carrier signal of the first and second electric TEST stimulation signals are configured to produce discrete IPCs at minimums in the modulation cycle.

In an embodiment, the recording is obtained using EEG. In an embodiment, the EEG system has two channels or three or more channels.

In an embodiment, the step of evaluating the recorded physiological responses of the user to the first and second TEST stimuli comprises providing an objective measure of the user's perception of said first and second TEST stimuli based on the recorded responses and extracting information about the current fitting of the first and second hearing assistance devices from said objective measure.

In an embodiment, the method comprises modifying the contra-lateral pulse train parameters, to "explore" the responses recorded by the recording system. In this context, "explore" refers to either the iterative modification of parameters from an a-priori known set of adaptively modify parameters according the response recorded after each set of parameters.

In an embodiment, the method comprises modifying the control parameter of the first pulse train, which is either dependent on the recorded responses or not. Modification occurs through means of either an adaptive procedure or a simple parameter exploration procedure.

In an embodiment, the method comprises modifying the setting of the processing unit (e.g. a speech processor) of the hearing assistance device(s) of the patient, in relation with the results of the methods mentioned above.

In an embodiment, the method of updating stimulus parameters relies on the evoked physiological response to periodic rapid transitions in the relative timing of the stimulation to each ear. As an example, a stimulus may alternate between having the same arrival time in both ears and having a delayed arrival time in one ear relative to the other. Different values of interaural timing difference may be presented, in a manner consistent with the method presented above. The method is applicable whether the stimulation is acoustical or electrical.

DEFINITIONS

In the present context, a 'hearing assistance device' refers to a device, such as e.g. a hearing instrument or an active ear-protection device or other audio processing device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A 'hearing assistance device' further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing assistance device may be configured to be worn in any known way, e.g. as a unit arranged behind the ear with a tube leading radiated acoustic signals into the ear canal or with a loudspeaker arranged close to or in the ear canal, as a unit entirely or partly arranged in the pinna and/or in the ear canal, as a unit attached to a fixture implanted into the skull bone, as an entirely or partly implanted unit, etc. The hearing assistance device may comprise a single unit or several units communicating electronically with each other.

More generally, a hearing assistance device comprises an input transducer for receiving an acoustic signal from a user's surroundings and providing a corresponding input audio signal and/or a receiver for electronically (i.e. wired or wirelessly) receiving an input audio signal, a signal processing circuit for processing the input audio signal and an output means for providing an audible signal to the user in dependence on the processed audio signal. In some hearing assistance devices, an amplifier may constitute the signal processing circuit. In some hearing assistance devices, the output means may comprise an output transducer, such as e.g. a loudspeaker for providing an air-borne acoustic signal or a vibrator for providing a structure-borne or liquid-borne acoustic signal. In some hearing assistance devices, the output means may comprise one or more output electrodes for providing electric signals.

In some hearing assistance devices, the vibrator may be adapted to provide a structure-borne acoustic signal transcutaneously or percutaneously to the skull bone. In some hearing assistance devices, the vibrator may be implanted in the middle ear and/or in the inner ear. In some hearing assistance devices, the vibrator may be adapted to provide a structure-borne acoustic signal to a middle-ear bone and/or to the cochlea. In some hearing assistance devices, the vibrator may be adapted to provide a liquid-borne acoustic signal to the cochlear liquid, e.g. through the oval window. In some hearing assistance devices, the output electrodes may be implanted in the cochlea or on the inside of the skull bone and may be adapted to provide the electric signals to the hair cells of the cochlea, to one or more hearing nerves, to the auditory cortex and/or to other parts of the cerebral cortex.

In an embodiment, 'a hearing assistance device' may comprise more than one output unit, e.g. two output units, e.g. an output transducer for converting an electric signal to an acoustic sound signal (or a vibrator for inducing bone conduction) and one or more electrodes for stimulation of a cochlear nerve. Such hybrid device for combined acoustic and electric stimulation of a user's ear/cochlea is relevant for users having residual hearing by means of stimulation via the eardrum and middle ear, cf. e.g. EP1522208A1.

A 'hearing assistance system' refers to a system comprising one or two hearing assistance devices, and a 'binaural or bilateral hearing assistance system' refers to a system comprising two hearing assistance devices and being adapted to provide audible signals to both of the user's ears. A 'binaural or bilateral hearing assistance system' may or may not have the capability of exchanging data between them. In an embodiment, a 'binaural or bilateral hearing assistance system' is adapted to establish a wireless link between the first and second hearing assistance devices. Alternatively or additionally, a 'binaural or bilateral hearing assistance system' may comprise a wired connection between the first and second hearing assistance devices, e.g. implanted in the scalp of the user, e.g. to combine two cochlear implant type hearing assistance devices. Hearing assistance systems or binaural/bilateral hearing assistance systems may further comprise 'auxiliary devices', which communicate with the hearing assistance devices and affect and/or benefit from the function of the hearing assistance devices. Auxiliary devices may be e.g. remote controls, audio gateway devices, mobile phones (e.g. SmartPhones), public-address systems, car audio systems or music players. Hearing assistance devices, listening systems or binaural listening systems may e.g. be used for compensating for a hearing-impaired person's loss of hearing capability, augmenting or protecting a normal-hearing person's hearing capability and/or conveying electronic audio signals to a person.

The disclosure is implemented in accordance with the dependent claims and in the detailed description of the invention.

As used herein, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element or intervening elements may be present, unless expressly stated otherwise. Furthermore, "connected" or "coupled" as used herein may include wirelessly connected or coupled. As used herein, the term "and/or" includes any and all combinations of one or more of the associated listed items. The steps of any method disclosed herein do not have to be performed in the exact order disclosed, unless expressly stated otherwise.

BRIEF DESCRIPTION OF DRAWINGS

The disclosure will be explained more fully below in connection with a preferred embodiment and with reference to the drawings in which.

The figures are schematic and simplified for clarity, and they just show details which are essential to the understanding of the disclosure, while other details are left out. Throughout, the same reference signs are used for identical or corresponding parts.

Figure 1A:
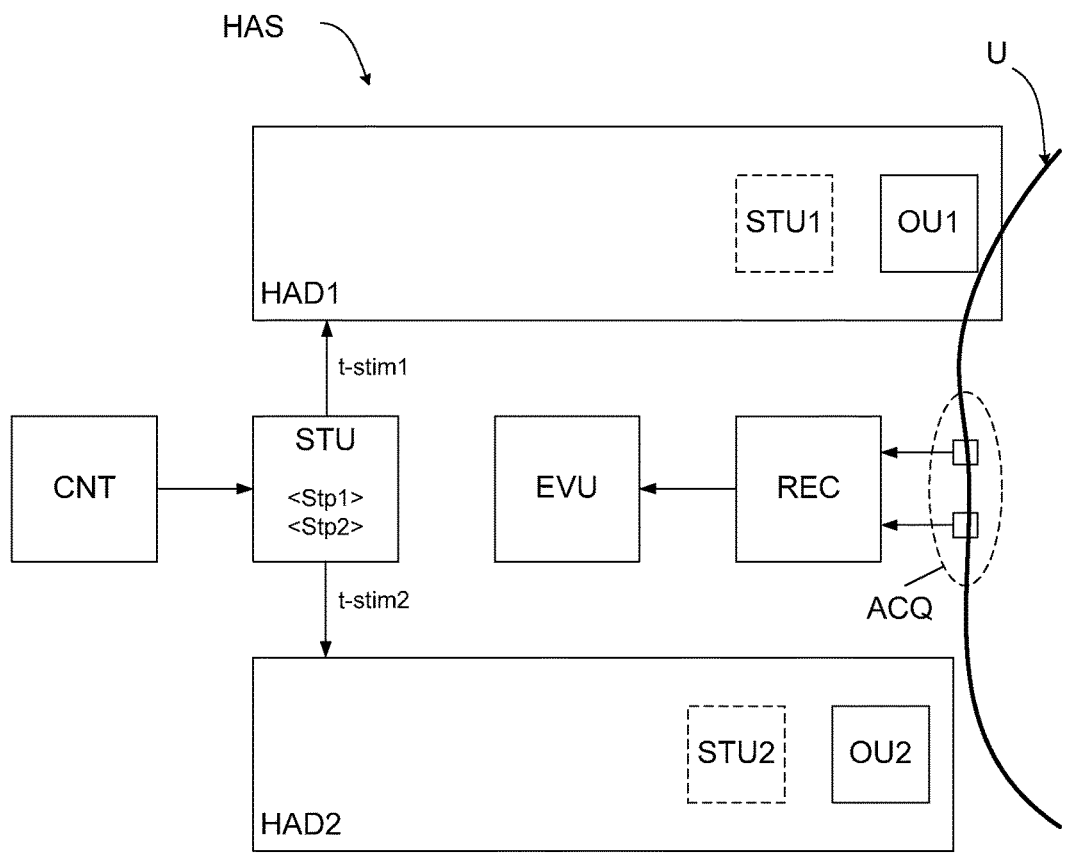
FIG. 1a shows a schematic illustration of a bilateral hearing assistance system according to an embodiment of the disclosure.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

Bilateral Cochlear Implant (CI) implantation attempts to improve speech perception and to restore binaural processing. However, several factors may reduce the binaural performance of bilaterally implanted CI users. For example, a place mismatch between the channels in each ear (cf. e.g. FIG. 2b) or electrode-neuron interface variations may have a negative impact on overall performance. While unilateral CI users can adapt to place-frequency mismatch, simulations in Normal Hearing (NH) listeners suggest that place mismatches across ears impair speech perception and are difficult to adapt to.

The present disclosure deals with measuring the response of the auditory system/brain to a signal that is designed to mimic an acoustic sound that moves from one side to the other relative to a listener's ears. This is achieved by the proposed method of designing stimulation signals and the accompanying measurement method. Measurement may be performed by external or internal electrodes picking up nerve responses, e.g. eCAPS from an electrode array implanted into the cochlea (e.g. using one electrode for stimulation and another one for recording of the eCAP-response). Alternatively, a diagnostic instrument may be used to pick up the user's response to the stimulation signal. An electric CI-stimulation may be given at both ears, or at one ear and an acoustic (or bone-vibrational) stimulation at the other ear.

The response to the applied signal is a periodic electrophysiological signal with a period equal to that of the abrupt phase changes, if the two hearing devices are equally fitted. This period is de-facto a sub-harmonic of the constant modulation that runs throughout the stimuli, since abrupt inter-aural phase changes occurs every N cycle of the steady modulation, where N is an integer. If, on the other hand, the applied signal is passing through non-fitted, i.e. with non-binaurally matched channels (electrodes), only the period of the constant modulation, unchanged during the entire stimuli will appear in the recorded signal.

Furthermore, it has to be noted that when the two channels are (binaurally) fitted (matched), the applied signal at both ears may be perceived to sense the movement from one side to the other. This occurs only when the steady modulation is slow enough and is not compulsory for the objective measure to work. One may use a steady modulation rates that are faster than binaural perception and still obtain a corresponding binaural ASSR-IPC. Binaural perception of change location is known to be a slow percept, a phenomenon known as binaural sluggishness. However, when the applied signals at both ears are not perceived as one signal at both ears, i.e. when the channels are not binaurally fitted, the measured electrophysiological response will be different, i.e. purely periodic at the steady modulation rate.

Finally, the two hearing devices can be considered to be (binaurally) fitted when a number of binaural channels can be obtained between the two ears, that number being either subset of all the devices' channels, or all possible binaural channels.

Figure 1B:
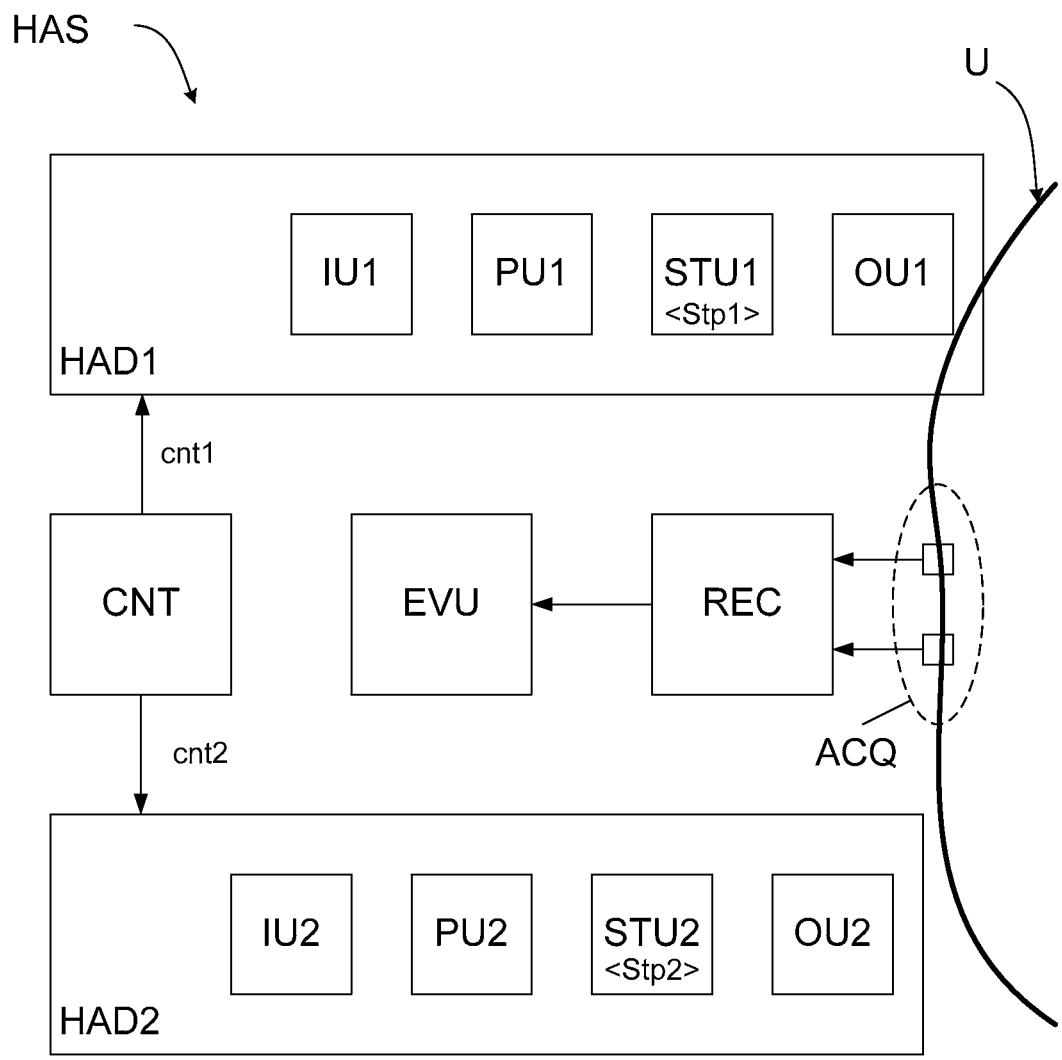
FIG. 1b shows a schematic illustration of a bilateral hearing assistance system according to an embodiment of the disclosure.
Figure 1C:
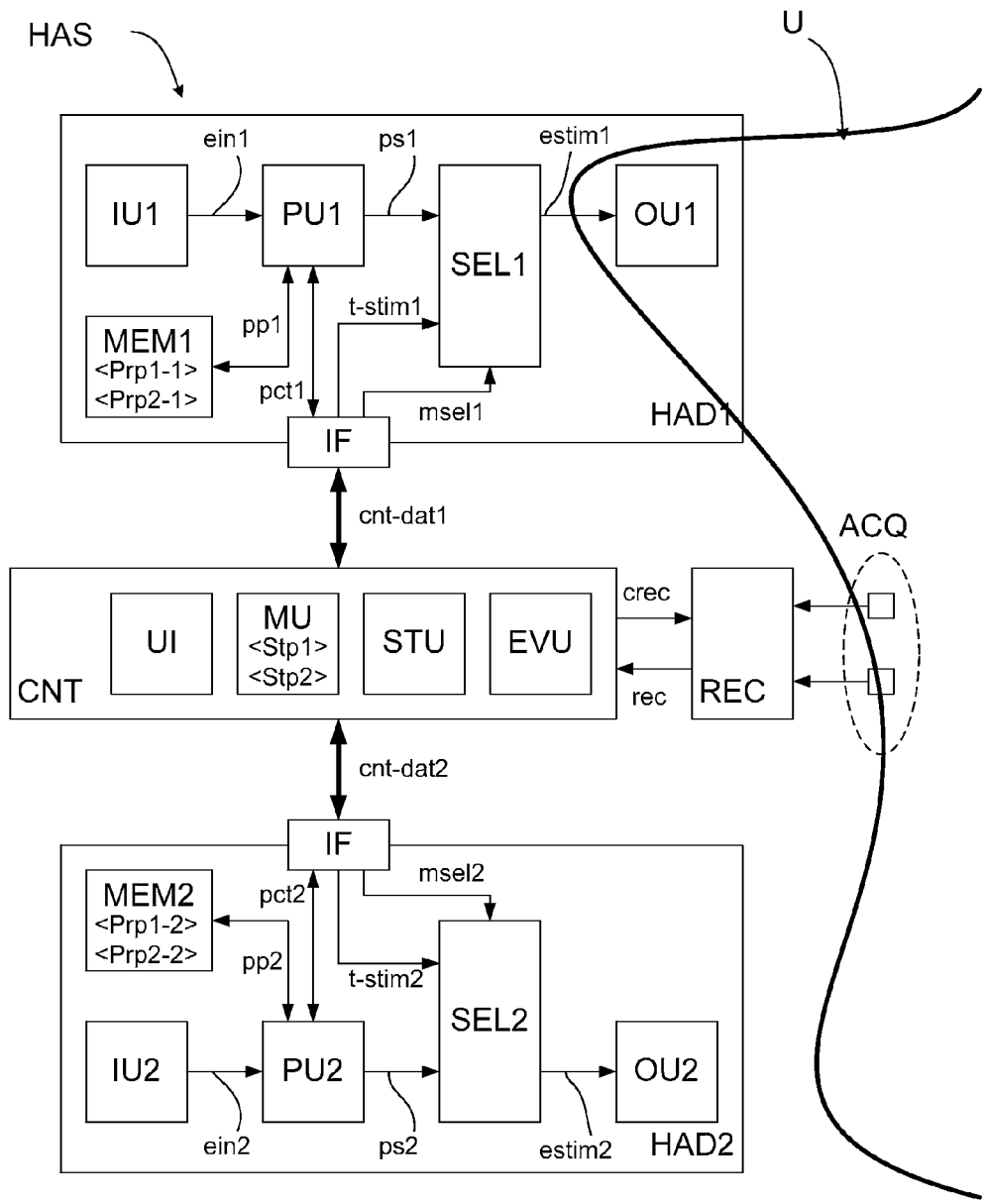
FIG. 1c shows a schematic illustration of a bilateral hearing assistance system according to an embodiment of the disclosure.

FIG. 1a, FIG. 1b, and FIG. 1c show in varying degree of detail three schematic illustrations of embodiments of a bilateral hearing assistance system according to the present disclosure.

FIG. 1a shows a bilateral hearing assistance system HAS comprising a control unit CNT and first and second hearing assistance devices HAD1, HAD2. The first and second hearing assistance devices are adapted for being located at or in an ear of the user U or to be partially or fully implanted in the head at an ear of the user. Each of the hearing assistance devices HAD1, HAD2 comprises an output unit OU1, OU2, respectively, adapted to present a stimulation signal to the user in a form allowing it to be perceived by the user U as an auditory signal. The system is configured to be operated in a NORMAL mode and a TEST mode. In the NORMAL mode each of the first and second hearing assistance devices HAD1, HAD2 are adapted to process an input audio signal based on configurable processing parameters and to provide a processed electric stimulation signal to its respective output unit OU1, OU2. The bilateral hearing assistance system HAS further comprises a stimulation unit STU for—in the TEST mode—delivering first and second electric TEST stimulation signals to the output units OU1 and OU2 of said first and second hearing assistance devices, respectively. The first and second electric TEST stimulation signals are preferably defined by respective first and second stimulation parameters, respectively. The electric TEST stimulation signals t-stim1, t-stim2 (or the respective stimulation parameters Stp1, Stp2) are e.g. stored in the stimulation unit STU (as indicated in FIG. 1a) and forwarded to the respective first and second hearing assistance devices controlled by the control unit CNT. The bilateral hearing assistance system HAS further comprises a recording unit REC configured to record the user's physiological response to the first and/or second electric TEST stimulation signals, and an evaluation unit EVU operationally connected to the recording unit. The evaluation unit EVU is configured to analyze the recorded physiological response of the user and to provide an objective measure of the user's perception of the TEST stimulation signals. The recording unit REC comprises an electrophysiological device comprising recording electrodes ACQ e.g. placed on the scalp, in an ear canal or in the head of the user. The electrophysiological device is configured to record the patient's physiological response evoked in the body (e.g. the brain) of the user by the electric TEST stimulation signals t-stim1, t-stim2. The recording electrodes may e.g. be placed on the scalp of the user to record small electrophysiological signals (e.g. EEG-electrodes adapted to pick up Auditor Brainstem responses (ABR)). Alternatively of additionally, the recording electrodes may be implanted in the head of the user, e.g. in or near cochlea (to pick up ECAPs). In an embodiment, the stimulation unit STU is fully or partially located in the first and second hearing assistance devices HAD1, HAD2 (cf. dashed units STU1, STU2) and electrically connected to the respective output units OU1, OU2 in the TEST mode to provide the respective electric TEST stimulation signals t-stim1, t-stim2.

FIG. 1b shows a second embodiment of a bilateral hearing assistance system HAS similar to the embodiment of FIG. 1a, but where the stimulation unit STU is distributed as units STU1, STU2 located in the first and second hearing assistance devices HAD1, HAD2, respectively. The first stimulation unit STU1 is configured to provide first electric TEST stimulation signals (e.g. defined by first stimulation parameters Stp1) to the first output unit OU1. Similarly, the second stimulation unit STU2 is configured to provide second electric TEST stimulation signals (e.g. defined by second stimulation parameters Stp2) to the second output unit OU2. The first and second hearing assistance devices HAD1, HAD2 comprise respective input units IU1, IU2 for receiving or providing electric input audio signals. The input units are operationally connected to respective processing units PU1, PU2 for—in the NORMAL mode of operation—are adapted to process the electric input audio signal (or a signal derived therefrom) based on configurable processing parameters and to provide a processed electric stimulation signal to respective output units OU1, OU2 of the first and second hearing assistance devices HAD1, HAD2. Hence, in the NORMAL mode of operation, each of the first and second hearing assistance devices HAD1, HAD2 are configured to process an input audio signal (from respective input units IU1, IU2, e.g. a microphone or a wired or wireless receiver of an electric audio signal) to provide a processed electric stimulation signal (e.g. providing a frequency dependent gain to compensate for a hearing impairment of the user) to its respective output unit OU1, OU2. The output units are adapted to present output stimuli representative of the respective input audio signals to the user for being perceived as corresponding (possibly enhanced) auditory signals. At least one of the output units OU1, OU2 (possibly both) may comprise a multi-channel electrode array implanted in the heard of user allowing electric stimulation of an electrode of the multi-channel electrode array to activate neurons of the auditory system of the user to evoke brain potentials (cf. FIG. 2, 3). One of the output units OU1, OU2 may comprise a loudspeaker for converting electric stimuli to acoustic sound signals. Alternatively, one of the output units OU1, OU2 may comprise a bone conduction vibrator for converting electric stimuli to mechanical vibration of the bones (e.g. the skull) of the user and for being perceived as a sound signal by the user's brain.

Various exemplary configurations of the bilateral hearing assistance system system include: In one embodiment, the stimulation unit on the ipsi-lateral side is a cochlear implant, and the stimulation unit on the contra-lateral side is a second cochlear implant. Both implants are controlled by independent processor units PUi. In another embodiment, the stimulation unit on the ipsi-lateral side is a cochlear implant, and the stimulation unit on the contra-lateral side is a second cochlear implant. Both implants are controlled by a shared processor unit. In a further embodiment, the stimulation unit on the ipsi-lateral side is a cochlear implant, and the stimulation unit on the contra-lateral side is a hearing aid is providing acoustical input to the user. In a further embodiment, the stimulation unit on the ipsi-lateral side is a cochlear implant, and the stimulation unit on the contra-lateral side is an auditory brainstem implant (ABI). In a further embodiment, the stimulation unit on the ipsi-lateral side is an auditory brainstem implant, and the stimulation unit on the contra-lateral side is an auditory brainstem implant (ABI). In an embodiment, the recording device is an electrophysiological device.

FIG. 1c shows a second embodiment of a bilateral hearing assistance system HAS similar to the embodiment of FIG. 1a, but where the control unit CNT comprises the stimulation unit STU. The control unit CNT further comprises a memory unit MU wherein stimulation parameters Stp1, Stp2 for defining or generating first and second electric TEST stimulation signals, respectively, are stored. The control unit CNT further comprises the evaluation unit EVU wherein an analysis of recorded physiological responses of the user is performed (either automatically according to predefined algorithms, or controlled by an operator) to provide an objective measure of the user's perception of the TEST stimulation signals. The control unit CNT further comprises a user interface UI allowing a user to influence or control the functionality of the hearing assistance system HAS. The user interface UI may e.g. e.g. allow the user U (or another person, e.g. an audiologist or a physician) to change a mode of operation, to initiate a stimulation procedure (activate the emission of TEST stimulation signals) and the subsequent recording of evoked responses. The use interface UI may further allow the modification of stimulation signals (e.g. from a number of predefined stimulation signals), to view resulting objective measures of the user's perception of the TEST stimulation signals. In a particular embodiment, the use interface UI may allow the modification of processing parameters of the processing units of the first and/or second hearing assistance devices HAD1, HAD2, e.g. based on an evaluation of the determined objective measure. The control unit CNT (e.g. the evaluation unit EVU is in communication with the recording unit REC via signals crec (control signal for controlling the recording of physiological responses) and rec (representing the physiological responses of the user). The recording unit REC comprises an electrophysiological device receiving inputs from or comprising capture electrodes ACQ (for—in the TEST mode—picking up evoked signals (potentials) in response to the TEST stimulation signals), the electrodes being located at or in the body (e.g. the head) of the user U.

The first HAD1 (and second HAD2) hearing assistance device (each) comprises a forward path comprising input unit IU1 (IU2) providing an electric input signal ein1 (ein2) to processing unit PU1 (PU2) providing processed signal ps1 (ps2) to selection unit SEL1 (SEL2), providing resulting electric stimulation signal estim1 (estim2) to output unit OU1 (OU2). The units IUi, PUi, SELi, OUi (i=1, 2) are operationally connected to each other to allow (in a NORMAL mode of operation) an input audio signal to be processed (enhanced according to a user's needs) and presented to the user U as a stimulus perceived by the user as an auditory signal. The output unit OW of hearing assistance device HAD1 is indicated to be located in the body (implanted in the head) of the user U, whereas the output unit OW of hearing assistance device HAD2 is indicated to be located outside the body (e.g. at or in an ear canal) of the user U.

Each of the first and second hearing assistance devices HAD1, HAD2 comprises a communications interface unit IF to the control unit allowing an exchange of data (including commands or control signals, cf. signals cnt-dat1, cnt-dat2) between the control unit and each of the hearing assistance devices. The interface units IF allow the control unit CNT to control a mode of operation of the bilateral hearing assistance system, in particular the first and second hearing assistance devices HAD1, HAD2. The mode of operation of the bilateral hearing assistance system HAS can be switched between a TEST mode and a NORMAL mode via mode control signals msel1 msel2 in the first and second hearing assistance devices HAD1, HAD2, respectively. In TEST mode, input signals t-stim1 and t-stim2 received from the control unit CNT via the communications interface units IF are selected as outputs of selector units SEL1 and SEL2 in the first and second hearing assistance devices HAD1, HAD2, respectively. In NORMAL mode, input signals ps1 and ps2 received from the processing units PU1 and PU2 are selected as outputs of selector units SEL1 and SEL2 in the first and second hearing assistance devices HAD1, HAD2, respectively.

Each of the first and second hearing assistance devices HAD1, HAD2 further comprises respective memory units MEM1, MEM2. A number of sets of processing parameters Prp1-1, Prp1-2, and Prp1-2, Prp2-2 for determining the processing of (an algorithm of) the processing unit PU1 and PU2 of the first and second hearing assistance devices HAD1, HAD2, respectively, are stored in the respective memory units MEM1, MEM2. The memory units MEM1 and MEM2 are operatively connected (via signals pp1 and pp2, respectively) to the respective processing unit PU1 and PU2, allowing the processing units to access the stored sets of processing parameters and to exchange a current set of processing parameters with a stored set of parameters. This allows the currently used processing parameters in processing units PU1 and PU2 of the first and second hearing assistance devices HAD1, HAD2, respectively, to be modified by the control unit CNT via the communications interface units IF. Alternatively, the current set of processing parameters in processing units PU1 and PU2 may be changed according to a predefined scheme in dependence on the results of the evaluation unit (objective measure of the user's perception of the TEST stimulation signals). The modification of processing parameters may be performed automatically according to a predefined algorithm, e.g. based on the information about the current fitting of the first and second hearing assistance devices extracted by the evaluation unit from the recorded physiological responses of the user (e.g. based on an objective measure). Alternatively or additionally, the modification of processing parameters may be performed via the user interface UI based on an interpretation of the recorded physiological responses of the user and/or the objective measure.

Figure 2A:
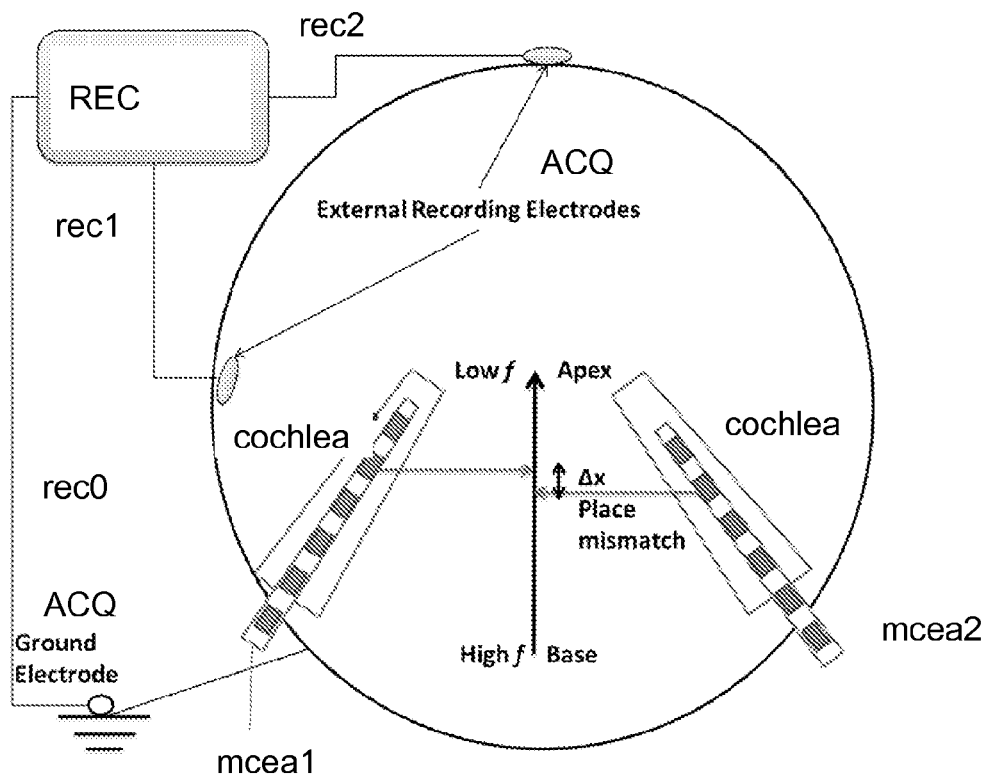
FIG. 2 shows a use scenario of an embodiment of a bilateral hearing assistance system according to the present disclosure, FIG. 2a illustrating an embodiment comprising two electrode arrays, one in each cochlea, FIG. 2b schematically illustrating an example of a location mismatch in cochlea of first and second multi-channel electrode arrays.
Figure 2B:
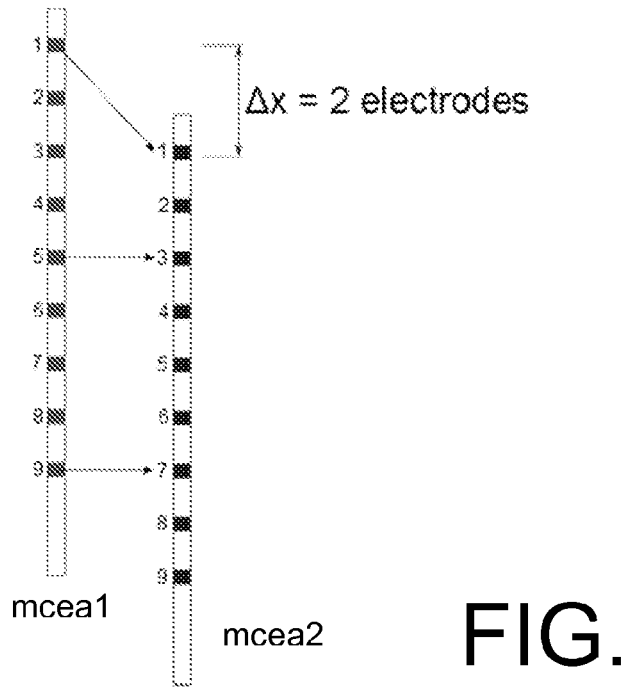

FIG. 2 shows a use scenario of an embodiment of a bilateral hearing assistance system according to the present disclosure, FIG. 2a illustrating an embodiment comprising two electrode arrays, one in each cochlea, FIG. 2b schematically illustrating an example of a location mismatch in cochlea of first and second multi-channel electrode arrays.

The embodiment of a bilateral hearing assistance system shown in FIG. 2a comprises first and second hearing assistance devices of the cochlear implant type, each device comprising an implanted part comprising a multi-channel electrode array mcea1, mcea2 implanted into or near a respective cochlear nerve. As illustrated in FIG. 2a, the first and second multi-channel electrode arrays mcea1, mcea2 are not identically or equivalently located with respect to cochlea or the cochlear nerve in question. There is a location mismatch that is indicated as Δx Place mismatch in FIG. 2a. As indicated in FIG. 2a at vertical arrow between the two schematically illustrated electrode arrays mcea1, mcea, the distant end (Apex in FIG. 2a) of cochlea represent the relatively lower frequencies (Low f in FIG. 2a), whereas the proximal end (Base in FIG. 2a) of cochlea represent the relatively higher frequencies (High f in FIG. 2a). The mismatch result in a less than optimal stimulation of the two electrode arrays, if not identified and compensated for, because stimuli intended for the same frequency range (same relative location of hair cells in cochlea at the two ears) are actually used to stimulate different frequency ranges, possibly leading to perceptual confusion by the user. The mismatch is further schematically illustrated in FIG. 2b, where electrode positions 1, 2, . . . , 9 on the first and second multi-channel electrode arrays mcea1, mcea2 are indicated. The physical mismatch is indicated to correspond to twice the basic distance between two neighbouring electrodes (assuming that the electrodes are equidistantly located on the carrier; this need not be the case, though). If e.g. the 9 electrodes divide the frequency range stimulated (e.g. 0-4 kHz), each electrode is on average responsible for a bandwidth of 450 Hz, so a mismatch of 'two electrodes' may incur considerable mismatch in the stimulated frequency ranges compared to the intention.

The embodiment of a bilateral hearing assistance system shown in FIG. 2a further comprises a recording system for recording a user's physiological response to the TEST stimulation signals. The recording system comprises recording unit REC electrically connected to recording (or acquisition) electrodes providing signals rec0, rec1, rec2 comprising evoked potentials from the user's body, e.g. brain wave signals. Three electrodes are shown, one being a reference electrode (denoted ACQ Ground Electrode in FIG. 2a). The electrodes may be external electrodes or alternatively implanted electrodes or a mixture. The two recording electrodes (denoted ACQ External Recording Electrodes in FIG. 2a) are indicated to be located on the head of the user (top electrode), e.g. in the scalp and inside the head (left electrode), respectively. These electrodes may alternatively be all implanted or all located externally.

The electric TEST stimulation signals applied to a selected pair of electrodes of the first and second multi-channel electrode arrays mcea1, mcea2 (e.g. electrode 1 on both arrays) may preferably comprise trains of pulses as described in connection with FIG. 4. The physiological response of the user to the applied electric TEST stimulation signals is recorded by the recording electrodes and signals rec0, rec1, rec2 are stored in the recording unit REC for later analysis. For a given electrode pair the applied stimuli may be adaptively modified (or changed according to a predefined scheme) to provide sufficient data for concluding whether or not a binaural perception of the user to given stimuli at a given electrode pair is detected. In a preferred embodiment, the method is based on recording frequency following response to abrupt interaural phase changes (FFR-IPCs) imposed on amplitude modulated stimulation signals (cf. FIG. 4). Consecutive (relevant) electrode pairs can be subsequently stimulated in the same manner. If a mismatch is detected, new pairs of electrodes can be simultaneously stimulated (e.g. electrode 1 of the first multi-channel electrode array with electrode 2 of the second multi-channel electrode array) and a better electrode pair match can be achieved, so that an optimal matching of electrode pairs can be arrived at.

Figure 3A:
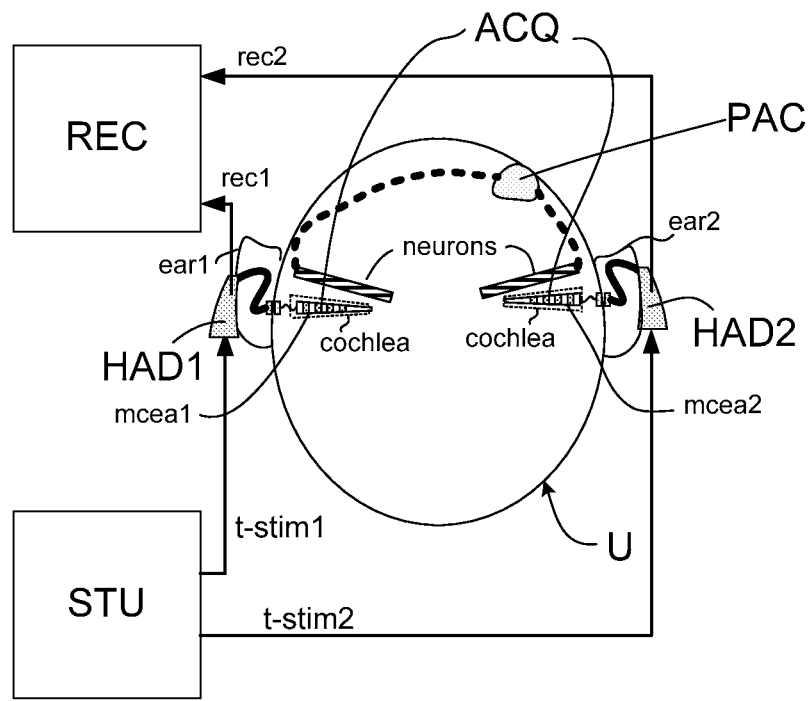
FIG. 3 shows two embodiments of bilateral hearing assistance systems, FIG. 3a illustrating a system comprising first and second hearing assistance devices of the a cochlear implant type, FIG. 3b illustrating a system comprising an air conduction type hearing assistance device and a cochlear implant type hearing assistance device.
Figure 3B:
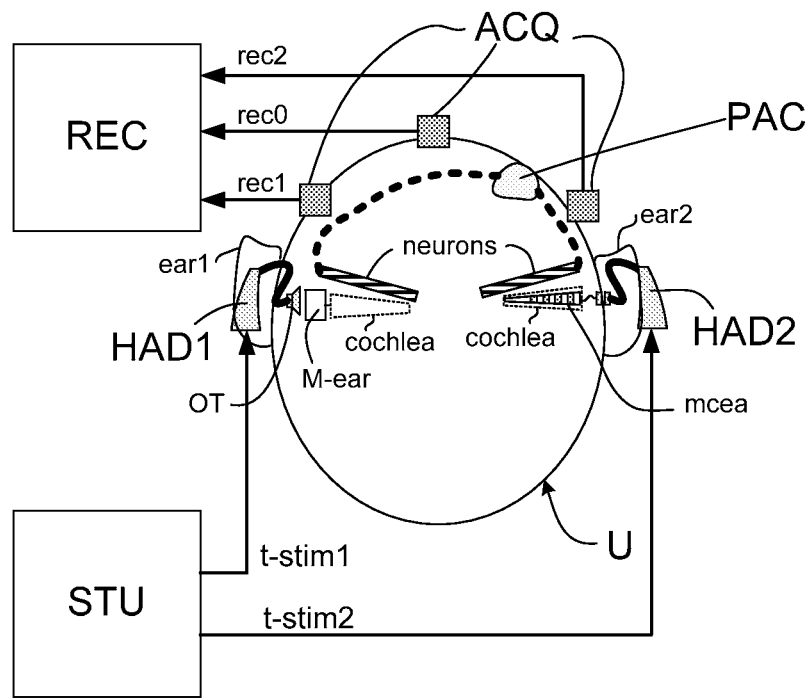

FIG. 3 shows two embodiments of bilateral hearing assistance systems, FIG. 3a illustrating a system comprising first and second hearing assistance devices of the a cochlear implant type, FIG. 3b illustrating a system comprising an air conduction type hearing assistance device and a cochlear implant type hearing assistance device.

The embodiment of a bilateral hearing assistance system shown in FIG. 3a is similar to the embodiment shown and discussed in connection with FIG. 2a. The bilateral hearing assistance system comprises first and second hearing assistance devices HAD1, HAD2 of the cochlear implant type, each device comprising an implanted part comprising a multi-channel electrode array mcea1, mcea2 implanted into or near a respective cochlear nerve. Each hearing assistance device further comprises one or more external parts, here a (BTE) part adapted to be located behind an ear (ear in FIG. 3) of the user U and a communication (COM) part adapted to be located on the head at an ear at a position allowing a (e.g. wireless) communication link to the implanted part to be established (including allowing the transfer of stimuli (or coded stimuli) to the multi-channel electrode array, possibly allowing the transfer of energy to the implanted part and possibly allowing the reception in the BTE part of data from the implanted part (e.g. nerve responses (eCAPs)). The BTE and COM parts are here shown to be electrically connected by a cable (indicated by a bold, curved connection in FIG. 3a). The locations of the first and second multi-channel electrode arrays mcea1, mcea2 in respective *cochleae* (denoted cochlea in FIG. 3a) in proximity of respective cochlear nerve (denoted neurons in FIG. 3a) are indicated in the drawing. The nerve connections from the respective cochlear nerves (neurons) to the auditory centre of the brain (the Primary Auditory Cortex, denoted PAC in FIG. 3) are indicated by the dashed curves in FIG. 3. The stimulation unit STU for generating or defining electric TEST stimulation signals to the respective output units of the first and second hearing assistance devices HAD1, HAD2 is indicated in FIG. 3, cf. signals t-stim-1, t-stim-2 from the stimulation unit STU to the (BTE part of the) respective hearing assistance devices. The recording unit REC receives evoked responses to the stimulation signals from the user U. In the embodiment of FIG. 3a, the evoked responses are recorded by implanted recording electrodes, cf. signals rec1 and rec2 from the respective first and second hearing assistance devices HAD1, HAD2. In an embodiment, the recording electrodes are located on the first and second multi-channel electrode arrays mcea1, mcea2 (e.g. near the currently stimulated electrodes).

The embodiment of a bilateral hearing assistance system shown in FIG. 3b is similar to the embodiment shown and discussed in connection with FIG. 3a, apart for the first hearing assistance device HAD1 being a hearing assistance device based on air conduction via the ear drum leading to stimulation of the middle ear (denoted M-ear in FIG. 3b) and cochlear. Further, the recording electrodes are shown to be externally located electrodes ACQ in the scalp of the user U. The recording unit receives signals rec0, rec1 rec2 from the three recording electrodes. In an embodiment, the electrode located at the top of the head is a reference electrode (signal rec0). The recording electrodes may alternatively be comprise a mixture or externally located and implanted electrodes (e.g. using the multi-channel array electrodes of the second (cochlear implant type) hearing assistance device HAD2. The output unit of the first hearing assistance device HAD1 is indicated to be an output transducer OT, here a loudspeaker for converting electrical stimuli to an output sound. It may alternatively comprise a (possibly bone anchored) vibrator of a bone conduction type hearing assistance device for converting electrical stimuli to a bone vibration configured to be perceived by the user as an auditory signal (sound).

The aim of the TEST-mode in case of a bilateral hearing assistance system comprising a) two cochlear implant type hearing assistance devices (FIG. 3a) or b) a mixed cochlear implant type and air or bone conduction type hearing assistance device (FIG. 3b) is the same. The aim is for the two hearing assistance devices HAD1, HAD2 of the bilateral hearing assistance system to agree on a stimulation scheme so that stimulation in a given frequency range of the frequency range of operation of the devices (e.g. 20 Hz to 4 kHz (or to 6 kHz or to 8 kHz or to 10 kHz) is also perceived by the user to be the same frequency range (in that a binaural effect is provided, where spatial cues can be perceived and increased speech intelligibility provided).

FIG. 4 shows various examples related to test stimulation signals comprising a train of pulses.

Figure 4A:
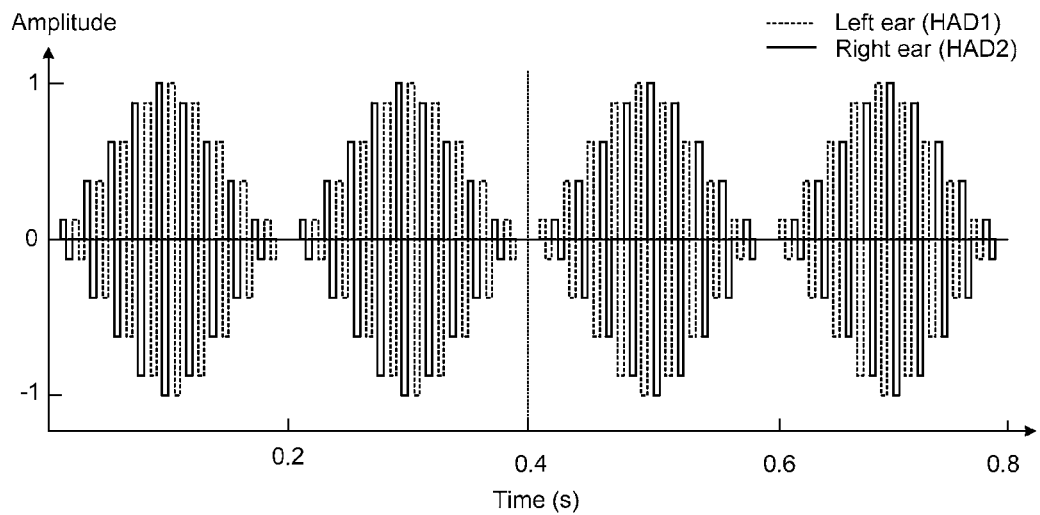
FIG. 4 shows various examples related to test stimulation signals comprising a train of pulses, FIG. 4a showing an embodiment of test stimulation signal comprising an amplitude modulated train of pulses, FIG. 4b illustrating an example of abrupt phase changes coded by different properties of a pulse train, and FIG. 4c illustrating three properties of the pulse trains, which can be used to encode modulation necessary for Auditory Steady State Responses (ASSR)

FIG. 4a shows an embodiment of test stimulation signal comprising an amplitude modulated train of pulses with a constant amplitude modulation rate of 50 Hz, and a sudden/abrupt inter-aural phase change every two amplitude-modulation cycles (i.e. an interaural phase change rate of 25 Hz). These abrupt interaural phase changes are performed during the modulation cycle at times where the modulated signal has minimum intensity. The steady modulation and the repeated abrupt interaural phase changes occur throughout the stimuli. Here only four such cycles of the steady modulation are shown while only one interaural phase change is shown.

Recordings were obtained using an EEG system with two channels. The phase of the carrier signal presented to each ear was manipulated to produce discrete IPCs (IPC=Interaural Phase Change) at minimums in the modulation cycle. IPCs were symmetrically opposed in each ear, and had an effective Interaural Phase Difference (IPD) that ranged between 11° and 135°. IPCs were presented at three different rates (3.4, 6.8, and 13.6 switches/s) and the carrier was modulated using several rates (27 to 109 Hz). Recordings demonstrated that frequency following response IPCs (FFR-IPC) could be obtained from all participants in all conditions. However, the Signal-to-Noise Ratio (SNR) was larger when IPCs were presented at 6.8 switches/s. On average, FFR-IPC were larger for IPDs in the range between 45° and 90°. Overall, FFR-IPC increased as the modulation rate increased. It is concluded that the FFR-IPC may be a suitable objective measure to match across-ear electrodes in bilaterally fitted CI users.

Auditory evoked responses will be elicited by delivering amplitude modulated stimuli where the phase difference between the stimuli being delivered to each ear will be abruptly changed at a minimum in the modulation cycle (cf. FIG. 4a). Preferably, parameters such as number of modulation cycles where the phase difference will be held constant, phase width, stimulation rate and interaural phase difference and stimulation amplitude are configurable, e.g. via a user interface and controlled by a researcher or clinician or audiologist, e.g. via (fitting) software.

FIG. 4a shows example stimuli (Amplitude (normalized scale between −1 and 1) versus Time (s, from 0 to 0.8 s, ~4 modulation cycles)) for left and the right ears (e.g. first and second hearing assistance devices/output units) in case of bilateral cochlear implant stimulation. In this example, the pulses presented to each ear have an interaural phase difference of 180°, with the right ear leading in the first two modulation cycles. After two modulation cycles (vertical line at Time=0.4 s), the phase is abruptly changed at the minimum of the modulation to −180°. This can be observed in FIG. 4a, where the left ear is leading after two modulation cycles (cf. abrupt change at time=0.4 s).

Stimuli will be presented in a steady-state fashion for epochs lasting for about 1 sec (an epoch being the length in time of a test sequence, e.g. the 4 cycles of FIG. 4a). Epochs will be presented in alternating polarity, i.e. the polarity of the pulse will be reversed for each epoch so that electrical artifacts will be minimized when averaging the epochs.

Fitting:

In order to match across-ear intra-cochlear electrodes, evoked responses will be recorded by delivering a stimulus (as shown in FIG. 4a) to a fixed intra-cochlear electrode in one ear. A second stimulus will be delivered in the opposite ear to one of several possible electrodes.

The selection of this second electrode will be adaptive; based on a bisection method, as explained in the following.

Thus, for a given static electrode position in one ear, three recordings will be taken, each from a different electrode in the opposite ear (e.g. electrodes 1, 5, and 9, potentially encompassing the whole array). From these three recordings, a new subinterval will be bisected by identifying the two out of three electrodes that showed the largest amplitude response. A new recording will then be taken from an electrode in the middle of the newly identified subinterval (e.g. electrode 7). The procedure will be repeated until the optimum position is identified, i.e. the electrode showing the largest evoked response.

This fitting procedure will be repeated three times, with three different fixed electrode positions in the first ear. More specifically, the position of the static intra-cochlear electrode will cover apical, middle and basal electrode locations in the cochlea. Hence, the procedure will provide three estimates of the offset of the two electrode arrays. Note that when the fixed electrode does not physically match an electrode in the opposite ear, the fitting will instead match the closest electrode in the opposite ear. This concept is illustrated in FIG. 2b. Static electrode number 1 (red array) would match to the same electrode in the opposite, despite the apparent offset. By measuring from fixed electrodes 5 and 9, the matched electrodes in the opposite ear are electrodes 3 and 7, respectively. Only in these two cases does the offset become apparent. Therefore, the estimation of the physical offset will be calculated by averaging the two largest electrode offsets.

Exemplary Recording Parameters:
  Biological magnitude (frequency) response: 100-500 nV
  Stimulation rates: The carrier may range between 0 to 1000 pps.
  Epoch length: it may vary depending on the desired frequency resolution. Usually, we would like a frequency resolution <1 Hz. This is particularly important for binaural interaction since the signal we are looking for are below 20 Hz. Thus, low frequency resolution will result in noisy frequency bins. If stimulation parameters can be fitted in the recording epoch (so that the period of both stimulus and modulation are integer multiples of the epoch), then averaged recorded epochs could potentially be concatenated to generate longer sweeps and so improving our frequency resolution. However, we need to remove the artifacts before concatenating the epochs. In any case, we will need to store continuously a time window (epoch), which allows us to save a full cycle for a 1-2 Hz signal, i.e. between 500 and 1000 ms.

Typical configuration: Reference electrode cz, active electrodes ipsi- or -contra-lateral. Ground can be placed on the clavicle or somewhere else.

Artifact rejection: Alternating polarity plus pulse blanking: Since the we are interested in a stationary response we need to measure a biological response which is overlapped by the electrical pulses. Therefore, alternating polarity and blanking are advantageous to observe the biological response.

Amplifier: The best is to use a DC amplifier to prevent artifact due to the filtering of the electrical pulses (see [Hofmann; 2010]).

Sampling Rate: The higher the better since we need to blank the electrical pulses. Fs>>16 kHz is suggested.

IPD/ITD values

May need IPD resulting on ITDs>100 μs (which have been reported as the threshold in CI users, cf. [Van Hoesel, 2007])

Figure 4B:
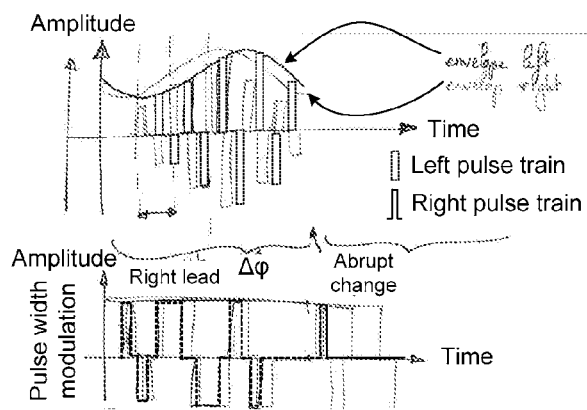

FIG. 4b illustrates an example of abrupt interaural phase changes while the periodic modulation of the pulse-train is either a pulse amplitude modulation (PAM), or pulse width modulation (PWM). The periodic modulation of the carrier pulse trains can be coded by different properties of a pulse train.

Figure 4C:
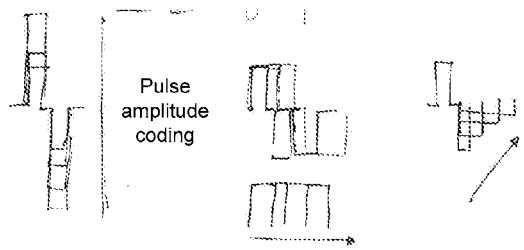

FIG. 4c illustrates three properties of the pulse trains, which can be used to encode modulation necessary for Auditory Steady State Responses (ASSR). In electric hearing, the perceived level of a sound is known to change with either modulation of the amplitude of a pulse, either their duration or also their pulse shape (ratio of time/amplitude of the anodic to cathodic phase). Each of these parameters offer possible modulation of the perceived intensity. For each parameter, the steady modulations vary between the lowest perceivable level and another level in the dynamic range of the channel. At the lowest perceivable level (e.g. zero-amplitude in the amplitude modulation—see FIG. 4a), the sudden change of interaural phase will produce the impression that the binaurally "merged" stimuli disappear and re-appear at another location.

Figure 5:
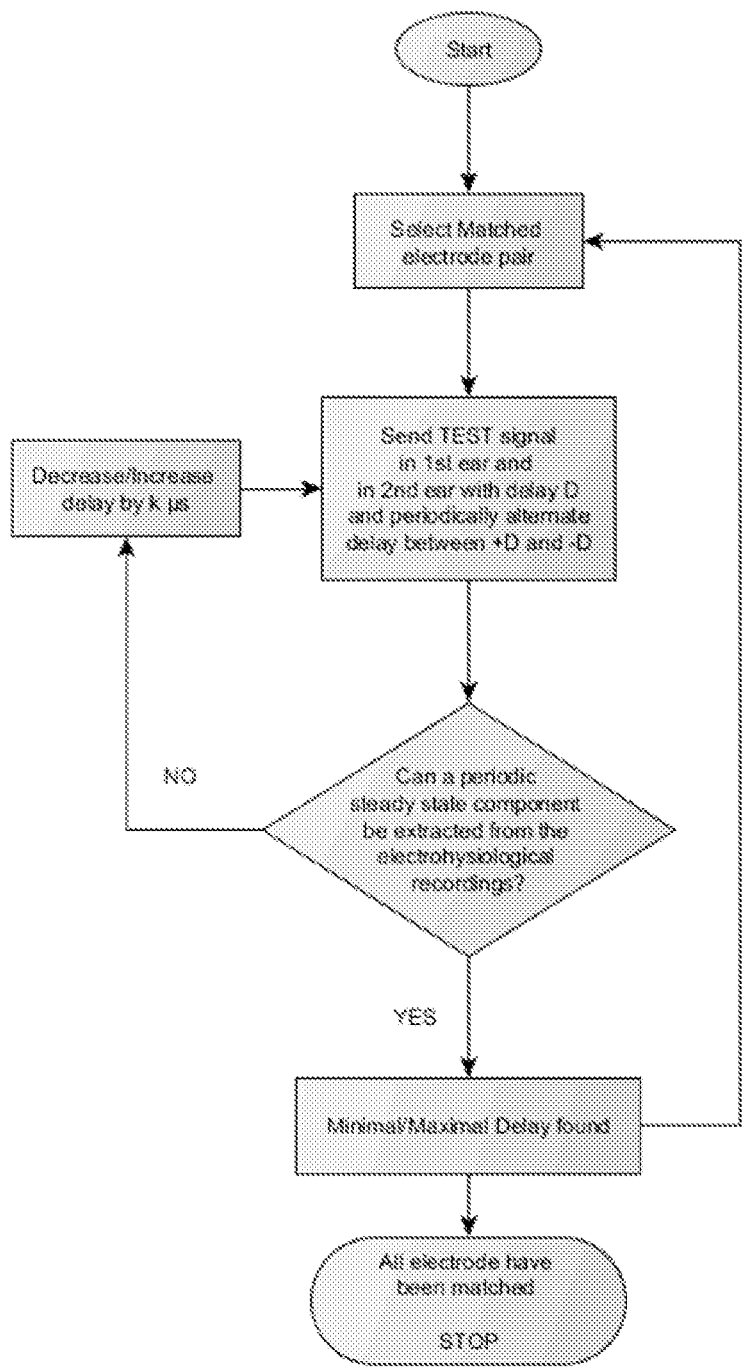
FIG. 5 shows a flow diagram of an embodiment of a method of fitting a bilateral hearing assistance system to a particular user, in particular relating to determining minimum or maximum delay between perception of a test signal at the left and right ears.

FIG. 5 shows a flow diagram of an embodiment of a method of fitting a bilateral hearing assistance system to a particular user, in particular relating to determining minimum or maximum delay between perception of a test signal at the left and right ears. The first and second hearing assistance devices are of the cochlear implant type comprising an implanted part with respective first and second multi-channel electrode array implanted into or near respective cochleae, as e.g. indicated in FIG. 3a. The method assumes that the bilateral hearing assistance system comprising first and second output units is operationally mounted at a user's left and right ears, respectively, and that the system is in a TEST mode, where (a) stimulation unit(s) for applying electric TEST stimulation signals is(are) connected to respective output units (multi-channel electrode arrays) of the first and second hearing assistance devices. The method comprises the following steps:

START.

S1. Select a pair of electrodes to be tested for matching, one from each of the first and second multi-channel electrode arrays.

S2a. Select first and second electric TEST stimulation signals. Set a start delay D between first and second electric TEST stimulation signals S2b. Apply selected first and second electric TEST stimulation signals to the first and second output units with delay D between the two signals.

S2c. Periodically alternate the delay between +D and −D.

S3. Record the user's physiological response to the applied electric TEST stimulation signals. (not shown in FIG. 5, implicit in Q1)

Q1. Can a periodic steady state component be extracted from the recorded electrophysiological responses?

Q1a. If NO: Go to Step S4: Change delay D according to a predetermined or adaptive algorithm. Go to Step S2b.

Q1b. If YES: Go to step S5: Identify minimum and/or maximum delay for which a periodic steady state component can be extracted from the recorded responses (binaural processing detected). Go to Q2.

Q2: Have all relevant electrode pairs been matched?

Q2a: If NO, go to step S1

Q2b: If YES, STOP.

Various methods of recording a user's response to the applied stimulation signals are available, typically in the form of some sort of brainwave signal mapping, e.g. based on voltage fluctuations due to neuron activity (e.g. EEG (ElectroEncephaloGraphy), eCAP-measurements) or magnetic fields (e.g. MEG (MagnetoEncephaloGraphy)), or magnetic resonance (MR) or nuclear magnetic resonance (NMR).

Figure 6:
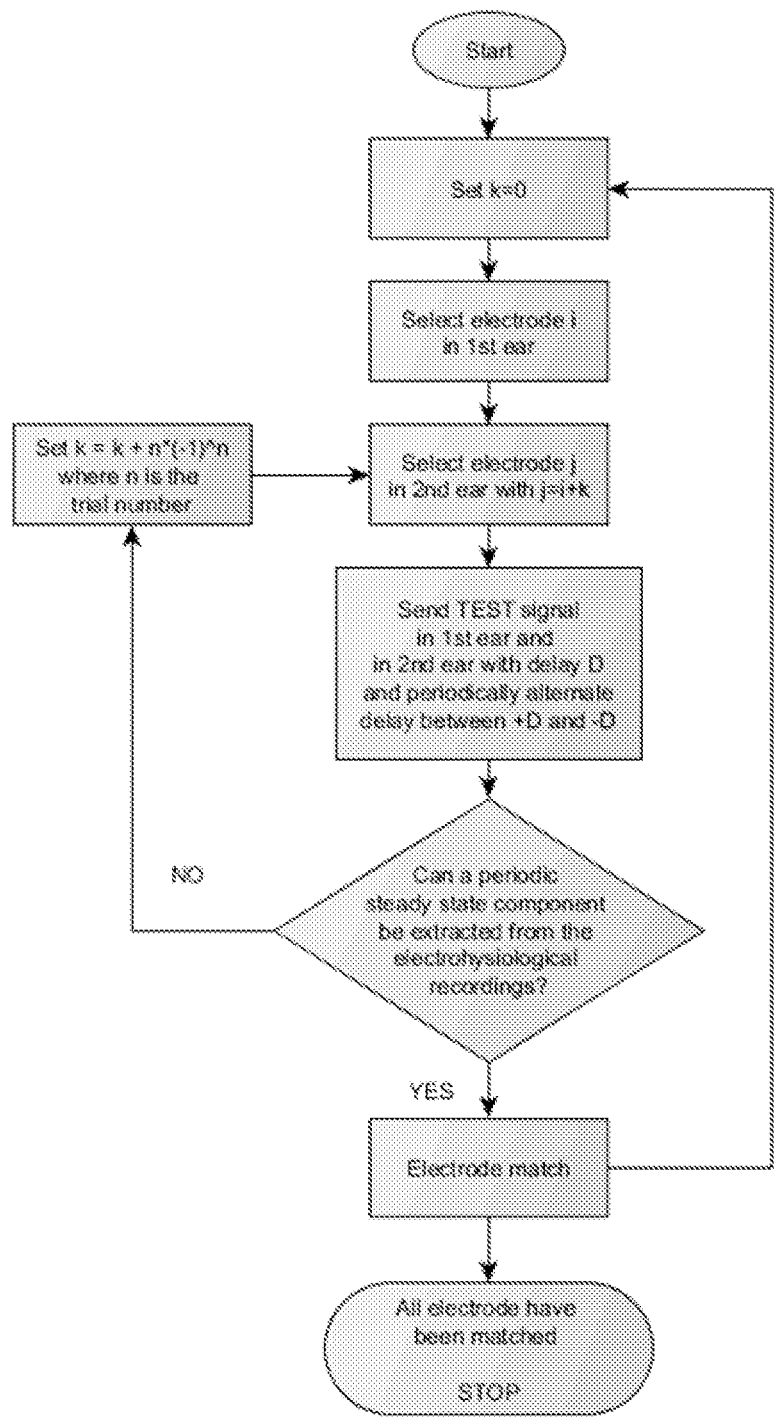
FIG. 6 shows a flow diagram of an embodiment of a method of fitting a bilateral hearing assistance system to a particular use, in particular relating to identification of an electrode mismatch in a bilateral cochlear implant hearing assistance system.

FIG. 6 shows a flow diagram of an embodiment of a method of fitting a bilateral hearing assistance system to a particular use, in particular relating to identification of an electrode mismatch in a bilateral cochlear implant hearing assistance system. The method exemplified in FIG. 6 assumes the same start conditions as noted in connection with FIG. 5. The method comprises the following steps:

START.

S1. Set electrode selection parameter k=0.

S2. Select electrode i in the first multi-channel electrode array.

S3. Select electrode j in the second multi-channel electrode array, j=i+k.

S4a. Select first and second electric TEST stimulation signals. Set a delay D between first and second electric TEST stimulation signals S4b. Apply selected first and second electric TEST stimulation signals to the first and second output units with delay D between the two signals.

S4c. Periodically alternate the delay between +D and −D.

S5. Record the user's physiological response to the applied electric TEST stimulation signals. (not shown in FIG. 6, implicit in Q1)

Q1. Can a periodic steady state component be extracted from the recorded electrophysiological responses?

Q1a. If NO: Go to Step S6: Change electrode selection parameter k according to a predetermined algorithm, e.g. $k=k+n\cdot(-1)^n$, where n is the trial number. Go to Step S3.

Q1b. If YES: Go to step S7: The current electrodes can be matched. Go to Q2.

Q2: Have all relevant electrode pairs been matched?

Q2a: If NO, go to step S1 (i=i+1)

Q2b: If YES, STOP.

The disclosure is implemented by the features of the independent claim(s). Preferred embodiments are defined in the dependent claims. Any reference numerals in the claims are intended to be non-limiting for their scope.

Some preferred embodiments have been shown in the foregoing, but it should be highlighted that the disclosure is not limited to these, but may be embodied in other ways within the subject-matter defined in the following claims and equivalents thereof.

REFERENCES

[Schaub; 2008] Arthur Schaub, Digital hearing Aids, Thieme Medical. Pub., 2008.
[Dajani & Picton; 2006] Dajani, H. R., & Picton, T. W. (2006). Human auditory steady-state responses to changes in interaural correlation. *Hearing Research,* 219(1-2), pp. 85-100.
[Dobie & Norton; 1980] Dobie, R. A., & Norton, S. J. (1980). Binaural interaction in human auditory evoked potentials. *Electroencephalography and Clinical Neurophysiology,* 49(3-4), pp. 303-13.
[Fowler & Horn; 2012] Fowler, C. G., & Horn, J. H. (2012). Frequency dependence of binaural interaction in the auditory brainstem and middle latency responses. *American Journal of Audiology,* 21(2), pp. 190-8.
[He, Brown & Abbas; 2012] He, S., Brown, C. J., & Abbas, P. J. (2012). Preliminary results of the relationship between the binaural interaction component of the electrically evoked auditory brainstem response and interaural pitch comparisons in bilateral cochlear implant recipients. *Ear and Hearing,* 33(1), pp. 57-68.
[Hofmann; 2010]
[Ishida & Stapells; 2009] Ishida, I. M., & Stapells, D. R. (2009). Does the 40-Hz auditory steady-state response show the binaural masking level difference? *Ear and Hearing,* 30(6), 713-715.
[Maki, Kawase & Kobayashi; 2009] Maki, A., Kawase, T., & Kobayashi, T. (2009). Effects of contralateral noise on 40-Hz and 80-Hz auditory steady-state responses. *Ear and Hearing,* 30(5), 584-9.
[Massoud et al.; 2011] Massoud, S., Aiken, S. J., Newman, A. J., Phillips, D. P., & Bance, M. (2011). Sensitivity of the human binaural cortical steady state response to interaural level differences. *Ear and Hearing,* 32(1), 114-20.
[Riedel & Kollmeier; 2006] Riedel, H., & Kollmeier, B. (2006). Interaural delay-dependent changes in the binaural difference potential of the human auditory brain stem response. Hearing Research, 218(1-2), 5-19.
[Ross; 2008] Ross, B. (2008). A novel type of auditory responses:
temporal dynamics of 40-Hz steady-state responses induced by changes in sound localization. *Journal of Neurophysiology,* 100(3), 1265-77.
[Ross, Tremblay & Picton; 2007] Ross, B., Tremblay, K. L., & Picton, T. W. (2007). Physiological detection of interaural phase differences. The *Journal of the Acoustical Society of America,* 121(2), p. 1017.
[Smith and Delgutte, 2008]
[Van Hoesel, 2007]

The invention claimed is:

1. A bilateral hearing assistance system comprising a control unit and first and second hearing assistance devices, each of the first and second hearing assistance devices being adapted for being located at or in an ear of the user or to be partially or fully implanted in the head at an ear of the user, and comprising an output unit adapted to present a stimulation signal to said user in a form allowing it to be perceived by the user as an auditory signal, the bilateral hearing assistance system further comprising one or more stimulation units for, in a TEST mode of operation of the hearing assistance system, delivering first and second electric TEST stimulation signals to said output units of said first and second hearing assistance devices, respectively;

a recording unit configured to record the user's physiological response to said first and/or second electric TEST stimulation signals; and an evaluation unit being configured to analyze the recorded physiological response of the user and to provide an objective measure of the user's perception of said TEST stimulation signals, wherein the first and second TEST stimuli comprise abrupt interaural phase changes (IPCs) imposed on amplitude modulated signals and wherein the recording of the user's physiological response comprises recording the Frequency Following Response to said interaural phase changes.

2. A bilateral hearing assistance system according to claim 1 wherein said control unit is configured to control said first and second electric stimulation signals.

3. A bilateral hearing assistance system according to claim 1 comprising a processing unit, which in a NORMAL mode of operation is adapted to process an input audio signal based on configurable processing parameters and to provide a processed electric stimulation signal to respective output units of the first and second hearing assistance devices.

4. A bilateral hearing assistance system according to claim 1 wherein the control unit is adapted to modify said first and second electric TEST stimulation signals based on said objective measure of the user's perception of said stimulation signals.

5. A bilateral hearing assistance system according to claim 3 configured to modify said configurable processing parameters of the first and/or second hearing assistance devices based on said objective measure of the user's perception of said TEST stimulation signals.

6. A bilateral hearing assistance system according to claim 1 wherein the first hearing assistance device comprises
a first implanted part adapted for being implanted in an ipsi-lateral side of the user's head, the implanted part comprising the output unit of the first hearing assistance device, and wherein said output unit comprises a first multi-channel electrode array adapted for being located in proximity of neurons of the auditory system of the user; and
a first electrode control unit configured to provide that a specific electrode in the first multi-channel electrode array is stimulated by said first electric TEST stimulation signal.

7. A bilateral hearing assistance system according to claim 6 wherein the second hearing assistance device comprises
a second implanted part adapted for being implanted in a contra-lateral side of the user's head, the implanted part comprising the output unit of the second hearing assistance device, and wherein said output unit comprises a second multi-channel electrode array adapted for being located in proximity of neurons of the auditory system of the user; and a second electrode control unit configured to provide that a specific electrode in the first multi-channel electrode array is stimulated by said second electric TEST stimulation signal.

8. A bilateral hearing assistance system according to claim 6 wherein the second hearing assistance device comprises an ear piece adapted for being located in or at an ear at a contra-lateral side of the user's head, the ear piece comprising the output unit of the second hearing assistance device, said output unit being adapted for converting said second electric TEST stimulation signal to an output sound and playing said output sound into the ear of the user.

9. A method of fitting a bilateral hearing assistance system to a particular user, the bilateral hearing assistance system comprising first and second hearing assistance devices, each being adapted for being located at or in an ear of the user or to be partially or fully implanted in the head at an ear of the user, each of the first and second hearing assistance devices being configured to allow electrical, mechanical or acoustic stimulation of the auditory system of the user, the method comprising generating first TEST stimuli to the auditory system at an ipsi-lateral side of the user's head;

generating second TEST stimuli to the auditory system at a contra-lateral side of the user's head;

recording the user's physiological response to either ipsi-lateral, contra-lateral, or bilateral stimulation;

evaluating the recorded physiological responses of the user to extract information about the current fitting of the first and second hearing assistance devices, wherein the first and second TEST stimuli comprise abrupt interaural phase changes (IPCs) imposed on amplitude modulated signals and where the recording of the user's physiological response comprises recording the Frequency Following Response to said interaural phase changes.

10. A method according to claim 9 comprising adapting processing parameters of the first and second hearing assistance devices based on the extracted information about the current fitting of the first and second hearing assistance devices.

11. A method according to claim 9 wherein the first and second hearing assistance devices each comprises a cochlear implant hearing assistance device.

12. A method according to claim 9 wherein first and second TEST stimuli each comprise a train of pulses.

13. A method according to claim 9 wherein the strength or the phase or both strength and phase of a steady-state auditory response produced by the first and second TEST stimuli is used to assess the optimality of the binaural fitting parameters.

14. A method according to claim 9 wherein the phase of the carrier signal of the first and second TEST stimuli are configured to produce discrete IPCs at minimums in the modulation cycle.

15. A bilateral hearing assistance system according to claim 2 comprising a processing unit, which in a NORMAL mode of operation is adapted to process an input audio signal based on configurable processing parameters and to provide a processed electric stimulation signal to respective output units of the first and second hearing assistance devices.

16. A bilateral hearing assistance system according to claim 2 wherein the control unit is adapted to modify said first and second electric TEST stimulation signals based on said objective measure of the user's perception of said stimulation signals.

17. A bilateral hearing assistance system according to claim 3 wherein the control unit is adapted to modify said first and second electric TEST stimulation signals based on said objective measure of the user's perception of said stimulation signals.

18. A bilateral hearing assistance system according to claim 4 configured to modify said configurable processing parameters of the first and/or second hearing assistance devices based on said objective measure of the user's perception of said TEST stimulation signals.

19. A bilateral hearing assistance system according to claim 2 wherein the first hearing assistance device comprises a first implanted part adapted for being implanted in an ipsi-lateral side of the user's head, the implanted part comprising the output unit of the first hearing assistance device, and wherein said output unit comprises a first multi-channel electrode array adapted for being located in proximity of neurons of the auditory system of the user; and a first electrode control unit configured to provide that a specific electrode in the first multi-channel electrode array is stimulated by said first electric TEST stimulation signal.

* * * * *